United States Patent
Koo et al.

(10) Patent No.: US 6,476,010 B2
(45) Date of Patent: Nov. 5, 2002

(54) METHOD FOR INCREASING INTESTINAL ABSORPTION OF FAT SOLUBLE VITAMINS IN POST-MENOPAUSAL WOMEN AND LOWER ANIMALS

(75) Inventors: Sung I. Koo, Manhattan; Kathy Lynn Gross, Topeka; Kevin Owen, Manhattan, all of KS (US)

(73) Assignees: Hill's Pet Nutrition, Topeka, KS (US); Kansas State Research Foundation, Manhattan, KS (US); Lonza Ltd., Basel (CH)

( * ) Notice: Subject to any disclaimer, the term of this patent is extended or adjusted under 35 U.S.C. 154(b) by 0 days.

(21) Appl. No.: 09/797,305

(22) Filed: Mar. 1, 2001

(65) Prior Publication Data

US 2001/0041695 A1 Nov. 15, 2001

Related U.S. Application Data

(60) Provisional application No. 60/188,419, filed on Mar. 10, 2000.

(51) Int. Cl.$^7$ ................... A61K 31/595; A61K 31/355; A61K 31/205; A61K 31/07

(52) U.S. Cl. ................. 514/168; 514/458; 514/556; 514/725

(58) Field of Search ............................... 514/168, 458, 514/556, 725

(56) References Cited

U.S. PATENT DOCUMENTS

| | | | |
|---|---|---|---|
| 4,382,092 A | 5/1983 | Cavazza | |
| 4,883,672 A | 11/1989 | Shug et al. | |
| 5,030,458 A | 7/1991 | Shug et al. | |
| 5,030,657 A | 7/1991 | Burtle et al. | |
| 5,223,264 A | 6/1993 | Wehling et al. | |
| 5,504,072 A | 4/1996 | Schmidl et al. | |
| 5,550,146 A | 8/1996 | Acosta et al. | |
| 5,560,928 A | 10/1996 | DeFelice | |
| 5,587,399 A | 12/1996 | Acosta et al. | |
| 5,661,123 A | 8/1997 | Stalker et al. | |
| 5,686,429 A | 8/1997 | Lin et al. | |
| 5,700,782 A | 12/1997 | Cope et al. | |
| 5,866,537 A | 2/1999 | Bianchi | |
| 5,916,912 A | 6/1999 | Ames et al. | |
| 5,976,568 A | 11/1999 | Riley | 424/451 |
| 5,977,162 A | 11/1999 | Seidman | |
| 6,204,291 B1 | 3/2001 | Sunvold et al. | |
| 2001/0000786 A1 | 5/2001 | Sunvold et al. | |

FOREIGN PATENT DOCUMENTS

| | | | |
|---|---|---|---|
| WO | WO 95/22259 | 8/1995 | |
| WO | WO 99 66913 A | 12/1999 | A61K/31/00 |
| WO | WO 99/66913 | 12/1999 | |

OTHER PUBLICATIONS

Research on the Menopause in the 1990's, WHO Technical Report Series #866 (1999).

Pola P, Savi L, Grill M, and Lago A. Carnitine in the Therapy of Dyslipidemic Patients, Curr. Ther. Res. 1980. 27: pp. 208–216.

Lacour B, Chanard J, Haguet M, DiGuilio S, et al. Carnitine Imporves Lipid Anomalies in Haemodialysis Patients, Lancet 1980. pp. 763–764.

Avogaro P, Bon GB, Cazzaloato G, Rorai E. Acute Effects on L–Carnitine on FFA and beta–hydroxy–butyrate in Man Pharmacol Res. Commun. 1981. 13: pp. 443–450.

Vacha GM, Giorcelli G, Silliprandi N, Corsi M. Favorable Effects of L–Carnitine Treatment on hypertriglyceridemia in hemodialysis patients: Decisive role of low levels of high density Lipoprotein–Chelosterol, Am J Clin Nutr 1983, pp. 532–540.

Arduini A, Dottori S, Sciarroni AF, et al. Effect of Propionyl–L–Carnitine treatment on membrane phospholipid fatty acid turnover in diabetic Rat Erythrocytes, Mol Cell Biochem 1995, pp. 31–37.

Arduini A, Bressen M, Sciarron F, et al. Carnitine palmitoyltransferase and acyl–CoA binding protein: two more players in the membrane phospholipid fatty acid turnover of human red cells. Biochemical Journal (1997), 325: pp. 811–814.

Adruni A, Holme S, Sweeney JD, et al. Addition of L–caratine to additive solution–suspended red cells stored at 4°C reduces in vitro hemolysis and improves in vivo viability. Transfusion, 1997, 37: pp. 166–174.

Schinetti ML, Rossini D, Greco R, Bertelli A. Protective action of acetylcarnitine on NADPH–inducded lipid peroxidation of cardiac microsomes. Drugs Exptl. Clin. Res. 1987, 8:pp. 509–515.

Calabrese V and Rizza V. Effects of L–carnitine on the formation of fatty acid ethyl esters in brain and peripheral organs after short–term ethanol administration in rat. Neurochemical Research, 1999, 24:pp. 79–84.

(List continued on next page.)

Primary Examiner—Raymond Henley, III
(74) Attorney, Agent, or Firm—Martin B. Barancik (57) ABSTRACT

The present invention provides a method for increasing the intestinal (lymphatic) absorption, cellular concentration, biliary secretion, hepatic storage, and/or liver concentration of a fat soluble vitamin in a post-menopausal woman. The method comprises orally administering to a post-menopausal woman in need thereof, a fat soluble vitamin and a fat soluble vitamin absorption increasing effective amount of L-carnitine. The L-carnitine enhances the antioxidant defense mechanism and lowers the risk of certain degenerative diseases, such as coronary heart disease, age-related macular degeneration, osteoporosis, cancer, and Alzheimer's, in post-menopausal women. The invention also provides a method for increasing the intestinal absorption of a fat soluble vitamin in an animal. The method comprises orally administering to the animal in need thereof, a fat soluble vitamin and a fat soluble vitamin absorption increasing effective amount of L-carnitine.

23 Claims, 3 Drawing Sheets

OTHER PUBLICATIONS

Paulson DJ, Shug AL, Zhao J. Protection of the ischemic diabetic heart by L-propionyl carnitine therapy. Molecular and Cellular Biochemistry, 1992, 116:pp. 131–137.

Kalaislvi T, Panneerselvam C. Effect of L-carnitine on the status of lipid peroxidation and antioxidants in aging rats. J. Nutr. Biochem., 1998, 9:pp. 575–581.

Bertelli A, Conte A, Ronca G. L-propionyl carnitine protects erythrocytes and low density lipoproteins against preosidation . . . Drugs Explt. Clin. Res., 1994, 20:pp. 191–197.

Hagan TM, Ingersoll RT, Wehr CM, et al. Acetyl–L-carnitine fed to old rats partially restores mitochondrial function and ambulatory activity. Proc National Academy of Sciences USA, 1998, 95:pp.9562–9566.

Hagen TM, Yowe DL, Bartholomew JC, et al. Mitochondrial decay in hepatocytes from old rats: membrane potential declines, heterogeneity and oxidants increase. Proc National Academy of Sciences USA, 1997, 94: pp. 3064–3069.

Hill K, The demography of menopause, Maturitas 1996, 23: pp. 113–127.

Chan AC. Vitamin E and Atherosclrosis, J Nutr 1998, 128:pp. 1593–1596.

Motoyama T, Kawano H, Kuggiyama K, et al. Vitamin E administratin improves impairment of endothelium–dependent vasodilation in patients with coronary spasmic angina. J Am Coll Cardiol 1998, 32:pp. 1672–1679.

Meydani M, Lipman RD, Han SN, et al. The Effect of Long–term Dietary Supplementation with Antioxidants, Ann NY Acad Sci 1998, 854:Seddon JM, Ajani UA, Sperduto RD, et al. Dietary carotenoids, vitamins A, C and E and advanced age–related macular degeneration. Eye disease case–control study group. JAMA 1994, 272:pp. 352–360.

Seddon JM, Ajani UA, Sperduto RD, et al. Dietary carotenoids, vitamins A, C and E, and advanced age–related macular degeneration. Eye disease case–control study group. JAMA 1994, 272: pp. 1413–1420.

West S, Vitale S, Hallfrisch J, et al. Are antioxidants or supplements protective for age–related macular degeneration? Arch Opthalmol 1994, 112: pp. 1413–1420.

Van der Hagen AM, Yolton DP, Kaminski MS and Yolton RL. Free radicals and antioxidant supplementation: a review of their roles in age–related macular degeneration. J Am Optom Assoc 1993, 112: pp. 222–227.

Golberg J, Flowerdew G, Smith E, Brody JA, Tso MO. Factors associated with age–related macular degeneration. An analysis of data from first National Health and Nutrition Examination Survey. Am J Epidemiol 1988, 128:pp. 700–710.

Sinclair AJ, Bayer AJ, Johnston J, Warner C, and Maxwell SR. Altered plasma antioxidant status in subjects with Alzheimer's disease and vascular dementia. Int. J. Geriatr Psychiatry 1998, 13: pp. 840–845.

Morris MC, Beckett LA, Scherr PA, Herbert LE, et al. Vitamin E and vitamin C supplement use and risk of incident Alzeheimer disease Alzheimer Dis Assoc Disord 1998, 12: pp. 121–126.

Subramaniam R, Koppal T, Green M, Yatin S, Jordan B, Drake J, and Butterfield DA. The free radical antioxidant vitamin E protects cortical synaptosomal membranes from amyloid beta–peptide (25–35) toxicity but not from hydroxynonenal toxicity: relevance to the free radical hypothesis of Alzheimer's disease. Neurochemical Research, 1998, 23:pp. 1403–1410.

Hills, *Prescription Diet Canine R/D*, late 1998.

Hills, *Prescription Diet Feline R/D*, late 1998.

METHOD FOR INCREASING INTESTINAL ABSORPTION OF FAT SOLUBLE VITAMINS IN POST-MENOPAUSAL WOMEN AND LOWER ANIMALS

RELATED APPLICATION

This application claims the benefit of U.S. Provisional application No. 60/188,419 filed Mar. 10, 2000.

FIELD OF THE INVENTION

This invention relates to a method for increasing the intestinal absorption, cellular concentration, biliary secretion, hepatic storage, and/or liver concentration of a fat soluble vitamin in a post-menopausal woman or a lower animal by orally administering L-carnitine and a fat soluble vitamin.

BACKGROUND OF THE INVENTION

L-carnitine plays a crucial role in the energy supply of tissues by modulating the entry of long-chain fatty acids into the mitochondrial matrix and their subsequent oxidation. Consistent with such a metabolic role, L-carnitine has been shown to be effective in lowering the serum levels of cholesterol, triglyceride, and free fatty acids, while increasing high density lipoprotein (HDL) cholesterol which is antiatherogenic. See Pola, P. et al., "Carnitine in the theraphy of dyslipemic patients", *Curr Ther Res* 27:208–16 (1980); Lacour, B. et al., "Carnitine improves lipid abnormalies in haemodialysis patients", *Lancet* 12:763–4 (1980); Avogaro, P., "Acute effect of L-carnitine on FFA and beta-hydroxybutyrate in man", *Pharmacol Res Commun* 13:433–50 (1981); and Vacha, G. M. et al. "Favourable effects of L-carnitine treatment on hypertriglyceridemia in hemodialysis patients: Decisive role of low levels of high density lipoprotein cholesterol", *Am J Clin Nutr* 38:532–40 (1983). Existing evidence indicates that L-carnitine and its esters enhance the stability and integrity of erythrocyte membranes by participating in the reacylation (repair) of membrane phospholipids subjected to oxidative damage. See Arduini, A. et al., "Effect of propionyl-L-carnitine treatment on membrane phospholipid fatty acid turnover in diabetic rat erythrocytes", *Mol Cell Biochem* 152:31–7 (1995); Arduini, A. et al., "Carnitine palmitoyltransferase and acyl-CoA binding protein: two more players in the membrane phospholipid fatty acid turnover of human red cells?", *Biochem J* 325:811–4 (1997); and Arduini, A. et al., "Addition of L-carnitine to additive solution-suspended red cells stored at 4° C. reduces in vitro hemolysis and improves in vivo viability", *Trandfusion* 37:166–74 (1997). It is of interest to note that such an action of L-carnitine and its esters is shown in the erythrocyte devoid of mitochondrial. L-carnitine supplementation to old rats has been shown to reverse the age-related decline in mitochondrial function, which may be linked to the membrane-stabilizing effect of L-carnitine. See Hagen, T. M. et al., "Acetyl-L-carnitine fed to old rats partially restores mitochondrial function and ambulatory activity", *Proc Natl Acad Sci USA* 95:9562–6 (1998). This finding is of particular significance in that oxidative damage to mitochondrial DNA increases markedly with age, leading to impaired cellular metabolism and function. See Hagen, T. M. et al., "Mitochondrial decay in hepatocytes from old rats: membrane potential declines, heterogeneity and oxidants increase", *Proc Natl Acad Sci USA* 94:3064–9 (1997).

Postmenopausal women make up over 15% of the total population in industrialized countries. By 2030, the proportion of postmenopausal women is predicted to increase to 23% of the total population. See Hill, K., "The demography of menopause", *Maturitas* 23:113–127 (1996). In addition, numerous epidemiological studies have shown that depletion of estrogen at the menopause influences cause-specific morbidity and mortality in later life. From the nutritional standpoint, the menopause is the time when the body's ability to absorb, assimilate, and metabolize nutrients begins to deteriorate. Consequently, the body status of nutrients is compromised at and after menopause, with the manifestations of specific nutrient deficiency symptoms with time.

It is well documented that postmenopausal women are substantially more susceptible to coronary heart disease, age-related macular degeneration, osteoporosis, cancer, and Alzheimer's disease. See Hill, K., "The demography of menopause", *Maturitas* 23:113–127 (1996). Although this is partly associated with the process of aging and deterioration of bodily functions and the immune systems, epidemiological evidence suggests that a significant association exists between the risks (or incidence) of certain chronic diseases and the inadequacies or deficiencies of specific nutrients in postmenopausal women. Current evidence strongly suggests that the compromised body status of lipid-soluble vitamins, such as vitamins A, D, and E, is a key factor influencing or contributing to the onset or development of the diseases. For example, the risk of coronary heart disease rises dramatically in postmenopausal and ovariectomized women, compared with women in their child-bearing years. Supplemental vitamin E has been shown to reduce significantly the risk of coronary heart disease by retarding the oxidation of serum lipoproteins and inhibiting the proliferation of vascular smooth muscle cells. See Chan, A. C., "Vitamin E and atherosclerosis", *J Nutr* 128:1593–6 (1998); Motoyama, T. et al., "Vitamin E administration improves impairment of endothelium-dependent vasodilation in patients with coronary spasmic angina", *J Am Coll Cardiol* 32:1672–9 (1998); and Meydani, M. et al., "The effect of long-term dietary supplementation with antioxidants", *Ann NY Acad Sci* 854:352–60 (1998). Also, it is well established that vitamin D deficiency is prevalent in postmenopausal women with increased risk for bone loss and osteoporosis. See WHO Scientific Group, "Research on the menopause in the 1990s", WHO Technical Report, Series 866, 1996, WHO, Geneva, Switzerland. Also, studies have shown that the incidence of age-related macular degeneration in postmenopausal women is inversely correlated with intakes of provitamin A (carotenoids) and vitamin E. See Seddon, J. M. et al., "Dietary carotenoids, vitamins A, C, and E, and advanced age-related macular degeneration. Eye disease case-control study group", *JAMA* 272:1413–20 (1994); West, S. et al., "Are antioxidants or supplements protective for age-related macular degeneration?", *Arch Opthalmol* 112:222–7 (1994); Van der Hagen, A. M., et al., "Free radicals and antioxidant supplementation: a review of their roles in age-related macular degeneration", *J Am Optom Assoc* 64:871–8 (1993); and Golberg, J. et al., "Factors associated with age-related macular degeneration. An analysis of data from first National Health and Nutrition Examination Survey", *Am J Epidemiol* 128:700–10 (1988). Furthermore, recent evidence suggests that oxidative stress may play an important role in the pathogenesis of Alzheimer's disease and that supplemental vitamin E may lower the risk of the disease. See Sinclair, A. J. et al., "Altered plasma antioxidant status in subjects with Alzheimer's disease and vascular dementia", *Int J Geriatr Psychiatry* 13:840–5 (1998); Morris, M. C., et al., "Vitamin E and vitamin C supplement use and risk of incident Alzheimer disease", *Alzheimer Dis Assoc Disord* 12:121–6 (1998);

Subramaniam, R. et al., "The free radical antioxidant vitamin E protects cortical synaptosomal membranes from amyloid beta-peptide (25–35) toxicity but not from hydroxynonenal toxicity: relevance to the free radical hypothesis of Alzheimer's disease", Neurochem Res 23:1403–10 (1998).

It has also been shown that cancer accounts for 47% of disease-related deaths in dogs followed by heart diseases (12%) and kidney diseases (7%). In cats, top ranking diseases include cancer (32%), kidney/urinary diseases (23%), and heart diseases (9%). See Morris Animal Foundation Animal Health Survey 1997. It is thought that these diseases in animals are associated with inadequate levels of certain vitamins, especially antioxidant vitamins like vitamin E and vitamin C, as well as vitamin A.

Therefore, there is a need for improving the nutritional status of the fat-soluble vitamins in postmenopausal women, particularly, considering the decreased efficiency of nutrient absorption and deterioration of the intestinal absorptive function with aging in general. There is also a need for improving the nutritional status of the fat-soluble vitamins in lower animals, particularly, considering deterioration of the intestinal absorptive function with aging in general.

SUMMARY OF THE INVENTION

The present invention provides a method for increasing the intestinal (lymphatic) absorption, cellular concentration, biliary secretion, hepatic storage, and/or liver concentration of a fat soluble vitamin in a post-menopausal woman. The method comprises orally administering to a post-menopausal woman in need thereof, a fat soluble vitamin and a fat soluble vitamin absorption increasing effective amount of L-carnitine. The L-carnitine enhances the antioxidant defense mechanism and lowers the risk of certain degenerative diseases, such as coronary heart disease, age-related macular degeneration, osteoporosis, cancer, and Alzheimer's, in post-menopausal women.

The invention also provides a method of reducing the risk of or preventing one or more diseases in a post-menopausal woman selected from coronary heart disease, agerelated macular degeneration, osteoporosis, cancer, and Alzheimer's. The method comprises orally administering to a post-menopausal woman in need thereof, a fat soluble vitamin and a fat soluble vitamin absorption increasing effective amount of L-carnitine.

The invention provides a method for increasing the intestinal absorption of a fat soluble vitamin in an animal. The method comprises orally administering to the animal in need thereof, a fat soluble vitamin and a fat soluble vitamin absorption increasing effective amount of L-carnitine.

The invention also provides a method of reducing the risk of or preventing one or more diseases in an animal selected from heart diseases, including coronary heart disease; kidney diseases; urinary diseases; and cancer. The method comprises orally administering to an animal in need thereof, a fat soluble vitamin and a fat soluble vitamin absorption increasing effective amount of L-carnitine.

DETAILED DESCRIPTION OF THE INVENTION

The present invention provides a method for increasing the intestinal absorption, cellular concentration, biliary secretion, hepatic storage, and liver concentration of a fat soluble vitamin in a post-menopausal woman. The method comprises orally administering to a post-menopausal woman in need thereof, a fat soluble vitamin and a fat soluble vitamin absorption increasing effective amount of L-carnitine.

In like matter, the intestinal absorption, cellular concentration, biliary secretion, hepatic storage, and liver concentration of a fat soluble vitamin can be increased in a lower animal, such as a cat or dog, by orally administering to a lower animal in need thereof, a fat soluble vitamin and a fat soluble vitamin absorption increasing effective amount of L-carnitine.

Suitable L-carnitines include, but are not limited to, L-carnitine; acyl-L-carnitines, such as acetyl L-carnitine, propionyl-L-carnitine, butanyl-L-carnitine, valeryl L-carnitine, and isovaleryl L-carnitine; pharmaceutically acceptable salts thereof; and any combination of any of the foregoing. Suitable pharmaceutically acceptable salts of L-carnitine include, but are not limited to, acetate, adipate, alginate, aspartate, benzoate, benzenesulfonate, bisulfate, bromide, butyrate, citrate, camphorate, camphorsulfonate, cyclopentanepropionate, chloride, digluconate, dodecylsulfate, ethanesulfonate, fumarate, glucoheptanoate, glucose phosphate, glycerophosphate, hemisulfate, heptanoate, hexanoate, iodide, 2-hydroxyethanesulfonate, lactate, maleate, methanesulfonate, methane sulphonate, 2-naphthalanesulfonate, nicotinate, orotate, oxalate, palmitate, pectinate, persulfate, 3-phenylpropionate, phosphate, picrate, pivalate, propionate, succinate, sulphate, tartrate, thiocyanate, tosylate, trichloroacetate, trifluoroacetate, and undecanoate salts and acid addition salts of L-carnitine. Preferably, the L-carnitine has low hygroscopicity. Preferred L-carnitine salts include, but are not limited to, L-carnitine L-tartrate, L-carnitine acid fumarate, L-carnitine adipate, and L-carnitine magnesium citrate.

For post-menopausal women, a fat soluble vitamin absorption increasing effective amount is. an amount of L-carnitine which increases the intestinal absorption of the fat soluble vitamin in a post-menopausal woman. In a post-menopausal woman, typically from about 10 mg to about 2 g of L-carnitine or pharmaceutically acceptable salt thereof per day and preferably from about 250 to about 750 mg of L-carnitine or pharmaceutically acceptable salt thereof per day is administered. More preferably, from about 400 to about 600 mg of L-carnitine or pharmaceutically acceptable salt thereof per day is administered to a post-menopausal woman. Generally, from about 50 to about 800 mg and preferably from about 100 to about 400 mg of L-carnitine or pharmaceutically acceptable salt thereof per 1,000 kcal of diet is administered to a post-menopausal woman. The term "diet" as used herein in reference to post-menopausal women is defined as the amount of food (in calories) consumed by a woman per day.

For a lower animal, e.g. mammals, a fat soluble vitamin absorption increasing effective amount is an amount of L-carnitine which increases the intestinal absorption of the fat soluble vitamin in an animal. The amount of L-carnitine administered to the lower animal may vary depending on age or disease condition of the animal. Generally, from about 1 to about 100 mg/kg of body weight, preferably from about 5 to about 75 mg/kg of body weight, and more preferably from about 5 to about 25 mg/kg of body weight of L-carnitine or pharmaceutically acceptable salt thereof is administered to a lower animal. Generally, from about 25 to about 5000 mg/kg of diet, preferably from about 50 to about 1000 mg/kg of diet, and more preferably from about 75 to about 500 mg/kg of diet of L-carnitine or pharmaceutically acceptable salt thereof is administered to a lower animal. The term "diet" as used herein for non-human (or lower) animals is defined as the amount of food (by weight) consumed by the animal per day.

Suitable fat soluble vitamins include, but are not limited to, vitamin A; vitamin D; vitamin E (and in particular α-tocopherol); their precursors, such as vitamin E acetate; esters having 1 to about 20 carbon atoms, such as vitamin A palmitate and vitamin E acetate; and any combination of any of the foregoing. According to one embodiment of the invention, the fat soluble vitamin is vitamin E. The term "vitamin E" as used herein includes α-, β-, δ-, and γ-tocopherols and their corresponding acylesters. The amount of a particular fat soluble vitamin administered daily to a post-menopausal woman may be that as recommend by the U.S. RDA published by the National Academy of Science. Typically, from about 8 to about 800 mg of vitamin E is administered daily to a post-menopausal woman. Preferably, from about 8 to about 400 mg of vitamin E is administered daily to a post-menopausal woman.

The amount of a particular fat soluble vitamin administered daily to a lower animal may be that as recommend by the various animal organizations. The amount of fat soluble vitamin administered may vary depending on age or disease condition of the animal and depending on the vitamin supplemented. Generally, from about 30 to about 5,000 international units (IU)/kg of diet and preferably from about 100 to about 1,000 IU/kg of diet of vitamin E is administered to a lower animal. Generally, from about 5,000 to about 1,000,000 IU/kg of diet and preferably from about 10,000 to about 500,000 IU/kg of diet of vitamin A is administered to a lower animal. Generally, from about 250 to about 10,000 IU/kg of diet and preferably from about 500 to about 3,000 IU/kg of diet of vitamin D is administered to a lower animal.

The lower animal may be a household pet, such as a cat or dog. Preferably, the animal is a spayed or neutered animal and in particular a spayed or neutered cat or dog.

Preferably, the L-carnitine and fat soluble vitamin are administered concurrently and more preferably in the same dosage unit form to the post-menopausal woman or lower animal. The L-carnitine and fat soluble vitamin are preferably administered during or after a meal.

Estrogen may also be administered to the post-menopausal woman with the L-carnitine and fat soluble vitamin to further enhance the antioxidant system of the post-menopausal woman. The amount of estrogen may be determined by methods known in the art of estrogen replacement therapy. Generally, from about 300 to about 600 μg of estrogen are administered with the L-carnitine and fat soluble vitamin to a post-menopausal woman.

Since L-carnitine in combination with fat soluble vitamins enhances the antioxidant defense mechanism, L-carnitine and a fat soluble vitamin may be administered to reduce the risk or prevent certain degenerative diseases, such as coronary heart disease, agerelated macular degeneration, osteoporosis, cancer, and Alzheimer's, in post-menopausal women. The method of the present invention may be used as a prolonged treatment, i.e. for months, years, or the rest of the person's life, to reduce the risk of acquiring the aforementioned diseases.

In like manner, L-carnitine may be administered to lower animals to reduce the risk or prevent certain degenerative diseases, such as heart diseases, including coronary heart disease; kidney diseases; urinary diseases; and cancer. The method of the present invention may be used as a prolonged treatment, i.e. for months, years, or the rest of the animal's life, to reduce the risk of acquiring the aforementioned diseases.

The L-carnitine, fat soluble vitamin, and, optionally, estrogen may be formulated into an oral dosage unit form for post-menopausal women, including, but not limited to, capsules, tablets, and particles, such as powders and sachets, by methods known in the art. The dosage unit form for post-menopausal women may be in liquid or solid form, but is preferably in solid form. The dosage unit form may further comprise additives including, but not limited to, a pH adjuster, a preservative, a flavorant, a taste-masking agent, a fragrance, a humectant, a tonicifier, a colorant, a surfactant, a plasticizer, a lubricant, a dosing vehicle, a solubilizer, an excipient, a diluent, a disintegrant, or any combination of any of the foregoing.

Also, for lower animals, the L-carnitine and fat soluble vitamin may be formulated into an oral dosage unit form, including, but not limited to, food, such as animal treats; capsules; tablets; and particles, such as powders and sachets, by methods known in the art. The L-carnitine and fat soluble vitamin may be administered to animals through food, water, animal treat, tablet, or capsule. The dosage unit form for lower animals may be in liquid or solid form. The dosage unit form may further comprise any of the aforementioned additives.

DESCRIPTION OF THE PREFERRED EMBODIMENTS

The following examples illustrate the invention without limitation. All parts and percentages are given by weight unless otherwise indicated.

EXAMPLE 1

Dietary Carnitine Increases the Liver Levels and Biliary Secretion of α-tocopherol in Ovariectomized Rats This study was conducted to determine if dietary carnitine affects the liver concentration and biliary secretion of α-tocopherol in ovariectomized rats.

Materials and Methods

Thirty two 10 weeks old female Sprague-Dawley rats weighing 214±6 g (Harlan Sprague Dawley, Indianapolis, Ind.) were placed individually in plastic cages with stainless steel wire-bottoms in a windowless room at a controlled temperature of about 23° C. and subjected to a light-dark cycle with the light period from 3:30 pm to 3:30 am and the dark period from 3:30 am to 3:30 pm. The rats were acclimatized for 1 week with free access to the deionized water and ad libitum fed a zinc-adequate AIN-93G diet (Reeves et al., J Nutr 1993;123:1939–1951) formulated by Dyets, Inc. (Bethlehem, Pa., USA) with 7% soybean oil as a fat source. Zinc carbonate was added to provide the desired levels of zinc. At the end of the first week, at the average body weight of 230±12 g, the rats were ovariectomized under halothane anesthesia after 16 hours of fasting. Initial blood samples (week 0) were taken from 5 randomly selected rats.

After 1 week of postoperative recovery, rats were divided into the following two experimental groups by matching body weight: One group of rats was fed a zinc-adequate AIN-93G diet containing $\alpha$-tocopherol-stripped soybean oil; 150 ppm Sipernat® 50, which is hydrated silica available from Degussa Corporation, Ridgefield, N.J.; and supplemented with 150 mg/kg L-carnitine. A control group was fed the same diet, except that the 150 mg/kg of L-carnitine was substituted with 150 ppm of $\alpha$-D-glucose. The normal food intake for both groups was around 15 g/day/rat. Blood samples were taken at the beginning of 1, 3, 5, 8 weeks from 5 randomly selected rats in each group.

At the end of the 8th week, bile duct cannulation was performed on the rats in both groups having an average body weight of about 340±15 g. Cannulation of the common bile duct was performed, following 16 hours food deprivation, as described previously (Noh et al., J Nutr Biochem 1999;10:110–117). Briefly, after performing a midline abdominal incision, the common bile duct was cannulated with PE-10 tubing (Clay Adams, Sparks, Md.) under halothane anesthesia (2.0% halothane in 2.01 oxygen/min). A silicone feeding catheter (Silastic medical grade tubing, Dow Coming, Midland, Mich.) was inserted into the gastric fundus region. The infusion catheter was exteriorized alongside the bile cannula through the right flank. Cannulated rats were placed in individual restraining cages and allowed to recover for at least 20 hours in a warm recovery chamber kept at about 30° C. Immediately after surgery, glucose-phosphate buffered saline (PBS) (in mmol/l: 277 glucose, 6.75 $Na_2HPO_4$, 16.5 $NaH_2PO_4$, 115 NaCl, and 5 KCI; pH 6.7) was continuously infused through the duodenal cannula at 3.0 ml/h via a syringe pump (Harvard Apparatus, Model 935, South Natick, Mass.).

After postoperative recovery, rats were infused with a lipid emulsion containing 565 $\mu$mol triolein (95%, Sigma Chemical, St. Louis, Mo.), and 396 $\mu$mol sodium taurocholic acid in 24 ml of PBS. Bile was collected hourly for 8 hours in pre-weighed conical centrifuge tubes containing 30 $\mu$g of n-propyl gallate in ice filled beakers. After bile collection, the rats were killed by cervical dislocation, and the livers were dissected. The samples were stored at about −70° C. until analysis.

Lipids were extracted by Folch's method (Folch et al., J Biol Chem 1957;226:497–509). The content of $\alpha$-tocopherol was determined as described by Zaspel et al. (Anal. Biochem. 1983;130:146–150). Briefly, 150 $\mu$L of bile and a certain amount of a-tocopherol acetate (as internal standard) were pipetted into a glass test. After acetone extraction, sodium sulfate drying, and centrifugation at 1000×g, the upper phase was filtered through a PTFE syringe filter (0.45 $\mu$m, Alltech Associates, Inc., Deerfield, Ill.), dried under $N_2$ gas and resolubilized in a defined volume of chloroform-methanol (1:3, v/v). The extracts were separated on a Beckman HPLC system having System Gold software (Beckman Instruments, Inc., Fullerton, Calif.) equipped with a C-18 reverse-phase column (Alltima C18, 5 $\mu$m, 4.6×150 mm, Alltech Associates, Inc., Deerfield, Ill.). Degassed methanol was used as the mobile phase at 2 ml/min. Typical retention times were 4.1 min for a-tocopherol and 5.3 min for a-tocopherol acetate. Detection was monitored at 292 nm (Module 166 UV-detector, Beckman Instruments). Alpha-tocopherol standard curve range was from 47.6 to 190.5 ng.

Statistical analyses were conducted using Excel 97 (Microsoft Inc, 1997) and PC SAS (SAS Institute, 1996). Student's t-test and a one-way ANOVA were used to compare group means. Differences were considered to be significant at $P<0.05$.

Results

Figure 1:
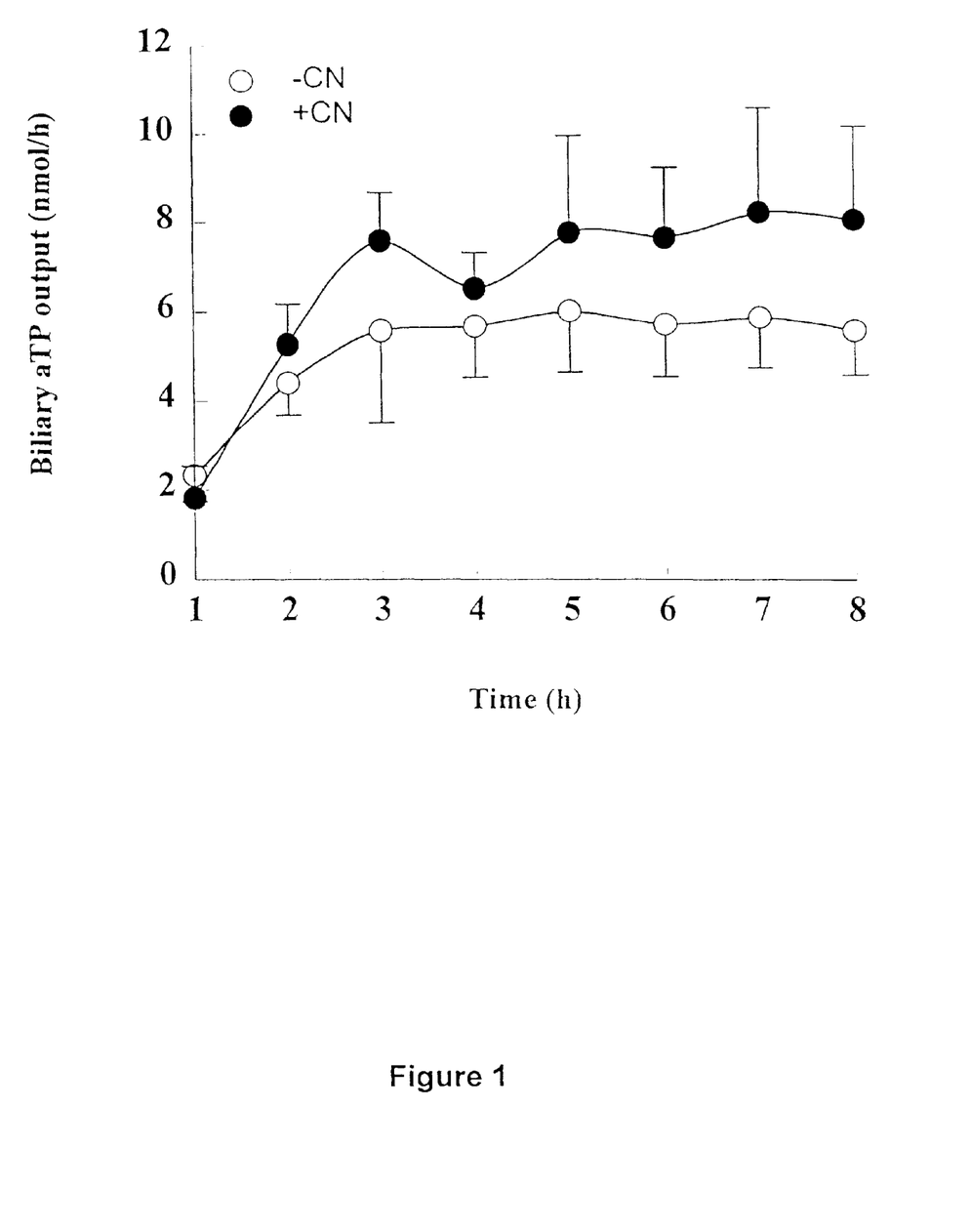
FIG. 1 is an illustration of biliary secretion of α-tocopherol (αTP) at hourly intervals for 8 hours. The control group is represented as −CN (i.e. without carnitine). The carnitine containing group is represented as +CN. All values are expressed as mean±standard deviation (SD). 5 rats were tested per time point (i.e. n=5).
Figure 2:
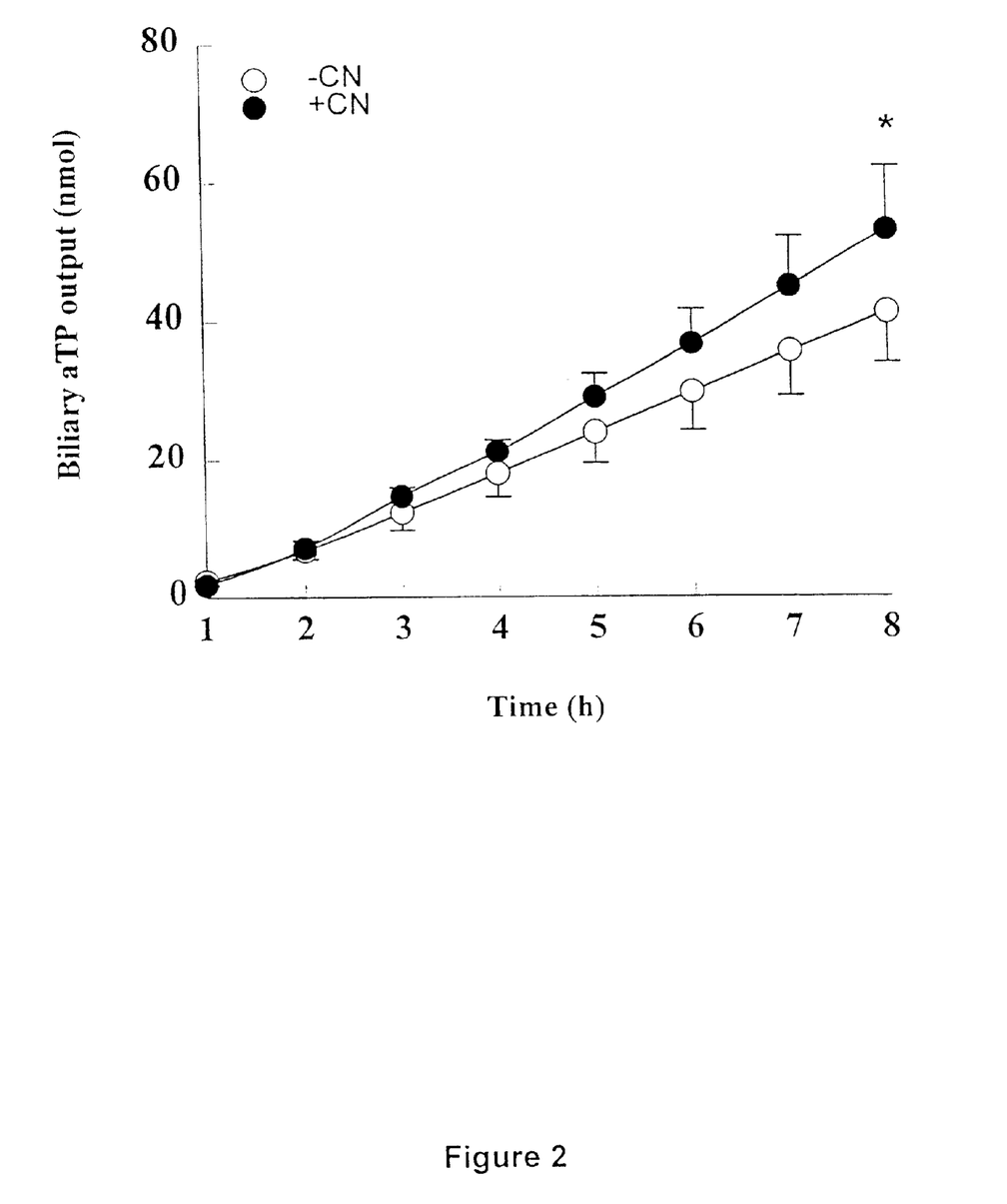
FIG. 2 is an illustration of cumulative biliary secretion of α-tocopherol (αTP) at hourly intervals for 8 hours. The control group is represented as −CN (i.e. without carnitine). The carnitine containing group is presented as +CN. All values are expressed as mean±SD. 5 rats were tested per time point (i.e. n=5). Asterisks (*) denote significant differences at p<0.05.

No difference was noted in bile flow (7.9±1.4 ml/8 hours in the carnitine group vs. 8.9±1.8 ml/8 hours in the control group). However, the biliary secretion of $\alpha$-tocopherol for 8 hours was significantly ($P<0.05$) higher in the carnitine group (53.1±9.3 nmol) than in the control group (41.3±7.3 nmol). FIGS. 1 and 2 graphically illustrate the output rate and cumulative output of $\alpha$-tocopherol, respectively. The liver concentration of $\alpha$-tocopherol was also significantly elevated in the carnitine group (129.6±19.5 nmol/g) compared with the control group (100.7±20.2 nmol/g). Likewise, the $\alpha$-tocopherol concentration per 100 mg total lipid was significantly higher in the rats fed a carnitine supplemented diet. The ratio of liver $\alpha$-tocopherol/phospholipid was significantly ($P=0.001$) higher in the carnitine group (4.8±0.6 nmol/$\mu$mol) than in the control group (3.3±0.4 nmol/$\mu$mol). These findings provide evidence that dietary carnitine improves the liver status of $\alpha$-tocopherol in ovariectomized rats.

EXAMPLE 2

Dietary Carnitine Enhances the Lymphatic Absorption of $\alpha$-tocopherol in Ovariectomized Rats This study was conducted to determine if dietary carnitine improves the intestinal absorption of $\alpha$-tocopherol in ovariectomized rats.

Materials and Methods

Thirty two 10 weeks old female Sprague-Dawley rats weighing 208±8 g (Harlan Sprague Dawley, Indianapolis, Ind.) were housed and fed as described in Example 1. At the end of second week, at the average body weight of 240±9 g, the rats were ovariectomized under halothane anesthesia after 16 hours fasting. Initial (0 week) blood samples were taken from 6 randomly selected rats.

Immediately after surgery, rats were divided into the following two experimental groups as described in Example 1, i.e., one group was fed a diet supplemented with carnitine, and one control group. The normal food intake for both groups was about 15–16 g/day/rat.

At the end of the $5^{th}$ week, Lymph duct cannulation was performed on each group having an average body weight of 340±15 g. Cannulation of the mesenteric lymph duct was performed, following 16 hours food deprivation, as described previously (Noh et al., supra). Briefly, after a midline abdominal incision was performed, the mesenteric lymph duct was cannulated with polyethylene tubing (SV 31 tubing, Dural Plastics, Auburn, Australia) by securing with a drop of cyanoacrylate glue (Krazy Glue, Columbus, Ohio) under halothane anesthesia (2.0% halothane in 2.01 oxygen/min). A silicone feeding catheter (Silastic medical grade tubing, Dow Coming, Midland, Mich.) was inserted into the gastric fundus region. The infusion catheter was exteriorized alongside the lymph cannula through the right flank. Cannulated rats were placed in individual restraining cages and allowed to recover for at least 20 hours in a warm recovery chamber kept at about 30° C. Immediately following surgery, glucose-phosphate buffered saline (PBS) (in mmol/l: 277 glucose, 6.75 $Na_2HPO_4$, 16.5 $NaH_2PO_4$, 115 NaCl, and 5 KCl; pH 6.7) was continuously infused through the duodenal cannula at 3.0 ml/h via a syringe pump (Harvard Apparatus, Model 935, South Natick, Mass.).

After postoperative recovery, rats were infused with a lipid emulsion containing 1 $\mu$Ci of [carboxyl-$^{14}$C]-triolein (specific activity 112.0 mCi/mmol, DuPont NEN, Boston, Mass.), 565 $\mu$mol triolein (95%, Sigma Chemical, St. Louis, Mo.), 3.56 $\mu$mol $\alpha$-tocopherol (all-rac-a-tocopherol, 97%, Aldrich Chemical, Milwaukee, Wis.), and 396 $\mu$mol sodium taurocholic acid in 24 ml of PBS. Lymph was collected hourly for 8 hours in pre-weighed conical centrifuge tubes containing 30 $\mu$g of n-propyl gallate and 4 mg of $Na_2EDTA$ in ice-filled beakers. After lymph collection, the rats were killed by cervical dislocation, and the livers were collected. The samples were stored at about –70° C. until analysis.

From the lipid extracted (Folch et al., supra), tissue total phospholipid was measured colorimetrically by the method of Reheja et al. (J Lipid Res 1973;14:695–697). Tissue total cholesterol was determined as described by Rudel et al. (J Lipid Res 1973;21:364–366). Alpha-tocopherol was determined as described by Zaspel et al (supra) and in Example 1 above. Statistical analyses were conducted as described in Example 1.

Results

Figure 3:
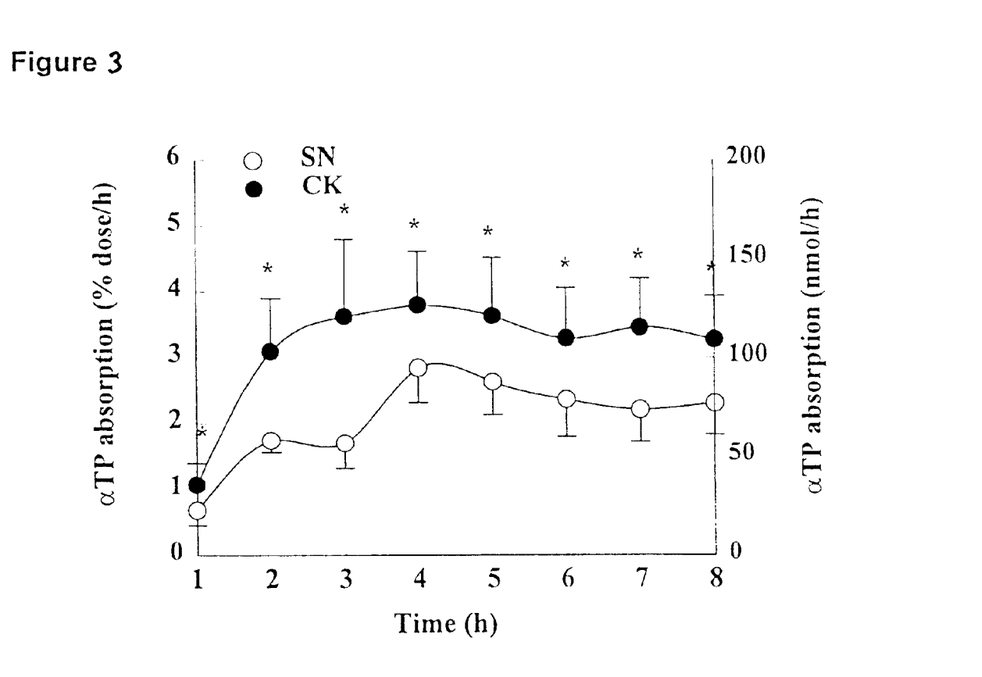
FIG. 3 is an illustration of lymphatic absorption of α-tocopherol (αTP) at hourly intervals for 8 hours. The control group is represented as SN. The carnitine containing group is represented as CK. All values are expressed as mean±SD. 5 rats were tested per time point (i.e. n=5). Asterisks (*) denote significant differences at p<0.05.
Figure 4:
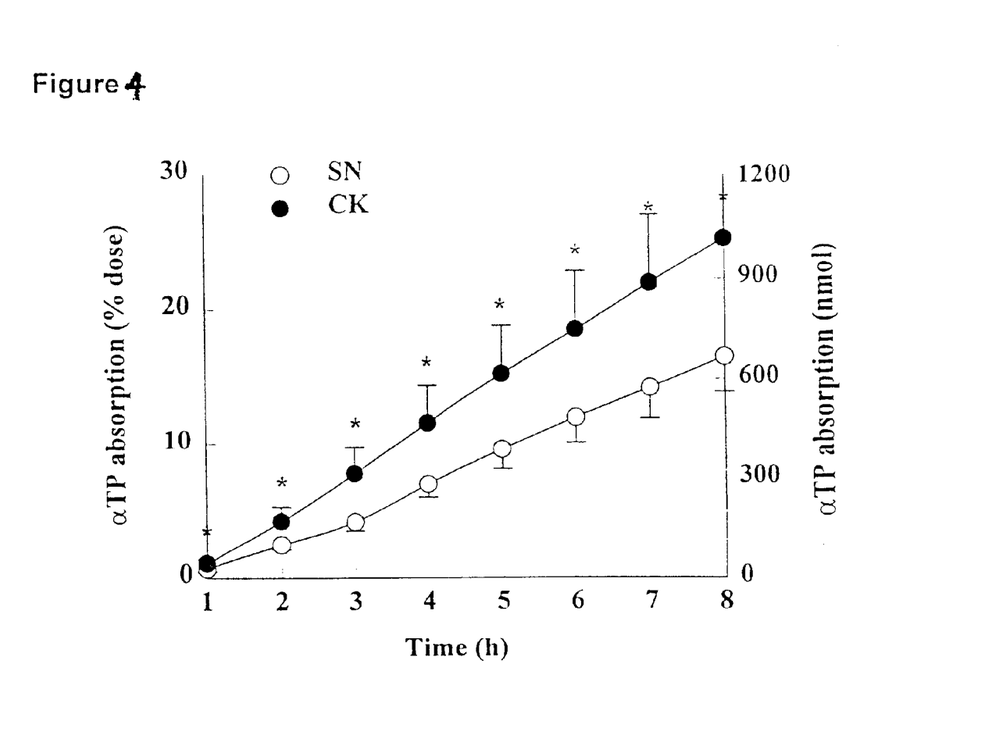
FIG. 4 is an illustration of cumulative lymphatic absorption of α-tocopherol (αTP) at hourly intervals for 8 hours. The control group is represented as SN. The carnitine containing group is CK. All values are expressed as mean±SD. 5 rats were tested per time point (i.e. n=5). Asterisks (*) denote significant differences at p<0.05.

No difference was noted in lymph flow (22.6±4.2 ml/8 hours in the carnitine group vs 24.5±2.5 ml/8 hours in the control group). The lymphatic absorption of $\alpha$-tocopherol for 8 hours was significantly ($P<0.05$) higher in the carnitine (899±200 nmol/8 h) than in the control group (587±92 nmol/8 hours). FIGS. 3 and 4 graphically illustrate hourly absorption rate and cumulative absorption of $\alpha$-tocopherol, respectively. The absorption of $^{14}$C-triolein was slightly increased ($P<0.05$) in the carnitine group (53.5±4.0% dose) compared with control rats (47.6±5.0% dose). Significant differences were noted in the ratios of lymph $\alpha$-tocopherol/phospholipid (46.9±8.8 nmol/$\mu$mol in the carnitine group vs 36.3±6.2 nmol/$\mu$mol in the control group), and of lymph $\alpha$-tocopherol/cholesterol (82.7±17.1 nmol/$\mu$mol in the carnitine group vs 60.8±6.0 nmol/$\mu$mol in the control group). These results present the first evidence that dietary carnitine increases the lymphatic absorption of $\alpha$-tocopherol.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A method for increasing the intestinal absorption of a fat soluble vitamin in a post-menopausal woman, the method comprising orally administering to a post-menopausal woman in need thereof, a fat soluble vitamin and a fat soluble vitamin absorption increasing effective amount of L-carnitine or a pharmaceutically acceptable salt thereof.

2. The method of claim 1, wherein the fat soluble vitamin is selected from the group consisting of vitamin A, vitamin D, vitamin E, and any combination of any of the foregoing.

3. The method of claim 2, wherein the fat soluble vitamin is vitamin E.

4. A method for increasing the intestinal absorption of a fat soluble vitamin in a post-menopausal woman, the method comprising orally administering to a post-menopausal woman in need thereof, from about 10 mg to about 2 g of L-carnitine or a pharmaceutically acceptable salt thereof per day and from about 8 to about 800 mg of vitamin E.

5. The method of claim 4, wherein the L-carnitine is L-carnitine L-tartrate, L-carnitine acid fumarate, L-carnitine adipate, or L-carnitine magnesium citrate.

6. The method of claim 4, wherein from about 250 to about 750 mg of L-carnitine is administered per day.

7. The method of claim 4, wherein from about 8 to about 400 mg of vitamin E is administered per day.

8. The method of claim 4, further comprising orally administering estrogen in combination with L-carnitine or a pharmaceutically acceptable salt thereof and the vitamin E.

9. A method for increasing the biliary secretion of a fat soluble vitamin in a post-menopausal woman, the method comprising orally administering to a post-menopausal woman in need thereof, a fat soluble vitamin and a fat soluble vitamin absorption increasing effective amount of L-carnitine or a pharmaceutically acceptable salt thereof.

10. A method for increasing the liver concentration of a fat soluble vitamin in a post-menopausal woman, the method comprising orally administering to a post-menopausal woman in need thereof, a fat soluble vitamin and a fat soluble vitamin absorption increasing effective amount of L-carnitine or a pharmaceutically acceptable salt thereof.

11. A method of reducing the risk of one or more diseases in a post-menopausal woman selected from coronary heart disease, age-related macular degeneration, osteoporosis, cancer, and Alzheimer's comprising orally administering to a post-menopausal woman in need thereof, a fat soluble vitamin and a fat soluble vitamin absorption increasing effective amount of L-carnitine or a pharmaceutically acceptable salt thereof.

12. A method for increasing the intestinal absorption of a fat soluble vitamin in an animal, the method comprising orally administering to the animal in need thereof, a fat soluble vitamin and a fat soluble vitamin absorption increasing effective amount of L-carnitine or a pharmaceutically acceptable salt thereof.

13. The method of claim 12, wherein from about 1 to about 100 mg of L-carnitine or a pharmaceutically acceptable salt thereof per kilogram of body weight per day is administered.

14. The method of claim 12, wherein from about 25 to about 5000 mg of L-carnitine or a pharmaceutically acceptable salt thereof per kilogram of diet per day is administered.

15. The method of claim 12, wherein from about 30 to about 5,000 IU. of vitamin E per kilogram of diet per day is administered.

16. The method of claim 12, wherein from about 5,000 to about 1,000,000 IU. of vitamin A per kilogram of diet per day is administered.

17. The method of claim 12, wherein from about 250 to about 10,000 IU. of vitamin D per kilogram of diet per day is administered.

18. The method of claim 12, wherein the fat soluble vitamin and L-carnitine or pharmaceutically acceptable salt thereof are administered in the form of a dosage unit form.

19. The method of claim 18, wherein the dosage unit form is a capsule, tablet, powder, or sachet.

20. The method of claim 12, wherein the animal is a household pet.

21. The method of claim 20, wherein the animal is a cat or a dog.

22. The method of claim 20, wherein the animal is spayed or neutered.

23. A method of reducing the risk of one or more diseases in an animal selected from heart diseases, kidney diseases, urinary diseases, and cancer, comprising orally administering to an animal in need thereof, a fat soluble vitamin and a fat soluble vitamin absorption increasing effective amount of L-carnitine or a pharmaceutically acceptable salt thereof.

* * * * *

UNITED STATES PATENT AND TRADEMARK OFFICE
CERTIFICATE OF CORRECTION

PATENT NO.   : 6,476,010 B2
DATED        : November 5, 2002
INVENTOR(S)  : Sung I. Koo, Kathy Lynn Gross and Kevin Owen It is certified that error appears in the above-identified patent and that said Letters Patent is hereby corrected as shown below:

Title page,
Item [73], Assignees, "Kansas State Research Foundation, Manhattan, KS (US)" should read -- Kansas State University Research Foundation --.

Signed and Sealed this

Fifth Day of August, 2003

JAMES E. ROGAN
*Director of the United States Patent and Trademark Office*

(12) EX PARTE REEXAMINATION CERTIFICATE (8425th)
United States Patent
Koo et al.

(10) Number: US 6,476,010 C1
(45) Certificate Issued: Jul. 26, 2011

(54) METHOD FOR INCREASING INTESTINAL ABSORPTION OF FAT SOLUBLE VITAMINS IN POST-MENOPAUSAL WOMEN AND LOWER ANIMALS

(75) Inventors: Sung I. Koo, Manhattan, KS (US); Kathy Lynn Gross, Topeka, KS (US); Kevin Owen, Manhattan, KS (US)

(73) Assignees: Hill's Pet Nutrition, Topeka, KS (US); Kansas State University Research Foundation, Manhattan, KS (US); Lonza Ltd., Basel (CH)

Reexamination Request:
No. 90/011,355, Nov. 29, 2010

Reexamination Certificate for:
Patent No.: 6,476,010
Issued: Nov. 5, 2002
Appl. No.: 09/797,305
Filed: Mar. 1, 2001

Certificate of Correction issued Aug. 5, 2003.

Related U.S. Application Data
(60) Provisional application No. 60/188,419, filed on Mar. 10, 2000.

(51) Int. Cl.
*A61P 5/30* (2006.01)
*A61P 9/00* (2006.01)
*A61P 9/10* (2006.01)
*A61P 13/00* (2006.01)
*A61P 13/12* (2006.01)
*A61P 19/10* (2006.01)
*A61P 25/28* (2006.01)
*A61P 27/02* (2006.01)
*A61P 35/00* (2006.01)
*A61P 43/00* (2006.01)
*A61P 1/16* (2006.01)
*A61P 3/00* (2006.01)
*A61P 3/02* (2006.01)
*A61K 47/18* (2006.01)
*A61K 9/14* (2006.01)
*A61K 9/28* (2006.01)
*A61K 9/48* (2006.01)
*A61K 31/07* (2006.01)
*A61K 31/205* (2006.01)
*A61K 31/355* (2006.01)
*A61K 31/565* (2006.01)
*A61K 31/59* (2006.01)
*A61K 31/592* (2006.01)
*A61K 31/593* (2006.01)
*A61K 31/185* (2006.01)
*A61K 31/352* (2006.01)

(52) U.S. Cl. .................. 514/168; 514/458; 514/556; 514/725

(58) Field of Classification Search .................. None
See application file for complete search history.

(56) References Cited

FOREIGN PATENT DOCUMENTS

WO   WO 99/66913 A2   12/1999

OTHER PUBLICATIONS

Martinková, J., et al., "Effect of Palmitoyl–DL–carnitine on the $^3$H–Dihydroergotoxine Intestinal Absorption in Rat," *Arzneim.—Forsch/Drug Res.* 40:145–149, Editio Cantor Aulendorf (1990).

Fix, J.A., et al., "Acylcarnitines: drug absorption–enhancing agents in the gastrointestinal tract," *Am. J. Physiol.* 251(3 Pt I):G332–G340, The American Physiological Society (1986).

Hutchinson–Williams, K.A., et al., "Estrogen Replacement Therapy (ERT) in High–Risk Cancer Patients," *Yale J. Biol. Med.* 64:607–626, The Yale Journal of Biology and Medicine, Inc. (1991).

Hidiroglou, M., et al., "Biokinetics and biliary excretion of radiotocopherol administered orally to sheep," *J. Anim. Sci.* 70(4):1220–1226, American Society of Animal Science (1992).

*Primary Examiner* — Bruce Campell (57) ABSTRACT

The present invention provides a method for increasing the intestinal (lymphatic) absorption, cellular concentration, biliary secretion, hepatic storage, and/or liver concentration of a fat soluble vitamin in a post-menopausal woman. The method comprises orally administering to a post-menopausal woman in need thereof, a fat soluble vitamin and a fat soluble vitamin absorption increasing effective amount of L-carnitine. The L-carnitine enhances the antioxidant defense mechanism and lowers the risk of certain degenerative diseases, such as coronary heart disease, age-related macular degeneration, osteoporosis, cancer, and Alzheimer's, in post-menopausal women. The invention also provides a method for increasing the intestinal absorption of a fat soluble vitamin in an animal. The method comprises orally administering to the animal in need thereof, a fat soluble vitamin and a fat soluble vitamin absorption increasing effective amount of L-carnitine.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-23 is confirmed.

* * * * *